(12) United States Patent
Busignies-Goddin et al.

(10) Patent No.: US 12,115,257 B2
(45) Date of Patent: Oct. 15, 2024

(54) NUCLEIC ACID VECTOR TABLETS

(71) Applicants: UNIVERSITE DE BORDEAUX, Bordeaux (FR); CENTRE NATIONAL DE LA RECHERCHE SCIENTIFIQUE, Paris (FR); INSTITUT POLYTECHNIQUE DE BORDEAUX, Talence (FR); ECOLE NATIONALE SUPERIEURE D'ARTS ET METIERS, Paris (FR); UNIVERSITÉ PARIS CITÉ, Paris (FR); PARIS SCIENCES ET LETTRES, Paris (FR); INSTITUT NATIONAL DE LA SANTÉ ET DE LA RECHERCHE MÉDICALE, Paris (FR)

(72) Inventors: Virginie Busignies-Goddin, Mérignac (FR); Pascal Bigey, Paris (FR); Christine Charrueau, Athis-Mons (FR); Virginie Escriou, Villejuif (FR); Pierre Tchoreloff, Gradignan (FR)

(73) Assignees: UNIVERSITÉ DE BORDEAUX, Bordeaux (FR); CENTRE NATIONAL DE LA RECHERCHE SCIENTIFIQUE, Paris (FR); INSTITUT POLYTECHNIQUE DE BORDEAUX, Talence (FR); ECOLE NATIONALE SUPERIEURE D'ARTS ET METIERS, Paris (FR); UNIVERSITÉ PARIS CITÉ, Paris (FR); PARIS SCIENCES ET LETTRES, Paris (FR); INSTITUT NATIONAL DE LA SANTÉ ET DE LA RECHERCHE MÉDICALE, Paris (FR)

(*) Notice: Subject to any disclaimer, the term of this patent is extended or adjusted under 35 U.S.C. 154(b) by 0 days.

(21) Appl. No.: 16/612,061

(22) PCT Filed: May 9, 2018

(86) PCT No.: PCT/EP2018/062141
§ 371 (c)(1),
(2) Date: Nov. 8, 2019

(87) PCT Pub. No.: WO2018/206723
PCT Pub. Date: Nov. 15, 2018

(65) Prior Publication Data
US 2020/0163879 A1    May 28, 2020

(30) Foreign Application Priority Data

May 10, 2017   (FR) .................................... 1754105

(51) Int. Cl.
*A61K 9/127* (2006.01)
*A61K 9/19* (2006.01)
(Continued)

(52) U.S. Cl.
CPC .............. *A61K 9/1272* (2013.01); *A61K 9/19* (2013.01); *A61K 9/2018* (2013.01); *A61K 31/7088* (2013.01); *A61P 1/04* (2018.01)

(58) Field of Classification Search
CPC ...... A61K 9/1272; A61K 9/19; A61K 9/2018; A61K 31/7088; A61P 1/04; A61P 15/02; A61P 1/00
See application file for complete search history.

(56) References Cited

U.S. PATENT DOCUMENTS

2006/0217345 A1* 9/2006 Matthes .................. A61P 31/12
                                                    514/49
2008/0213377 A1* 9/2008 Bhatia ................ A61K 49/0067
                                                    424/489
(Continued)

FOREIGN PATENT DOCUMENTS

CA     2564525    * 11/2005
CA     2724173    * 11/2009
(Continued)

OTHER PUBLICATIONS

Shim, G., et al In Asian Journal of Pharmaceutical Science, 8, pp. 72-80, 2013.*
(Continued)

*Primary Examiner* — Gollamudi S Kishore
(74) *Attorney, Agent, or Firm* — SALIWANCHIK, LLOYD & EISENSCHENK (57) ABSTRACT

The invention relates to a process for the manufacture of a tablet comprising a nucleic acid vector.

19 Claims, 7 Drawing Sheets

(51) Int. Cl.
    *A61K 9/20*     (2006.01)
    *A61K 31/7088*     (2006.01)
    *A61P 1/04*     (2006.01)

(56) References Cited

U.S. PATENT DOCUMENTS

| | | | |
|---|---|---|---|
| 2011/0027293 A1* | 2/2011 | Munawar | A61K 38/02 424/159.1 |
| 2011/0028535 A1 | 2/2011 | Kubota et al. | |
| 2012/0220760 A1* | 8/2012 | Ushida | A01K 67/0276 536/23.7 |
| 2014/0199371 A1* | 7/2014 | Bancel | A61K 31/7115 424/450 |
| 2016/0194368 A1* | 7/2016 | Hoge | C12N 15/63 424/450 |
| 2017/0007702 A1* | 1/2017 | Heyes | A61P 1/16 |
| 2020/0163879 A1 | 5/2020 | Busignies-Goddin et al. | |

FOREIGN PATENT DOCUMENTS

| | | |
|---|---|---|
| EP | 1 080 733 | 3/2001 |
| EP | 1 920 765 | 5/2008 |
| EP | 3 621 596 | 3/2020 |
| JP | 2-78623 | 3/1990 |
| KR | 20150127582 | * 11/2015 |
| WO | WO 99/61003 | 12/1999 |
| WO | WO 03/017940 | 3/2003 |
| WO | WO 03/099261 | 12/2003 |
| WO | WO 2015/128030 | 9/2015 |

OTHER PUBLICATIONS

Kundu, A.K., et al In Int J Pharm Feb. 28, 423 (2), pp. 525-534. Feb. 28, 2012.*

Written Opinion in International Application No. PCT/EP2018/062141, Aug. 27, 2018, pp. 1-5.

Monteleone, G. et al. "Mongersen, an Oral SMAD7 Antisense Oligonucleotide, and Crohn's Disease" *The New England Journal of Medicine*, 2015, pp. 1104-1113, vol. 372, No. 12.

Tillman, L. G. et al. "Oral Delivery of Antisense Oligonucleotides in Man" *Journal of Pharmaceutical Sciences*, Jan. 2008, pp. 225-236, vol. 97, No. 1.

Busignies, V. et al. "Compression of Vectors for Small Interfering RNAs Delivery: Toward Oral Administration of siRNA Lipoplexes in Tablet Forms" *Mol. Pharmaceutics*, 2020, pp. 1159-1169, vol. 17.

Raoof, A. A. et al. "Oral Bioavailability and Multiple Dose Tolerability of an Antisense Oligonucleotide Tablet Formulated with Sodium Caprate" *Journal of Pharmaceutical Sciences*, Jun. 2004, pp. 1431-1439, vol. 93, No. 6.

Lindahl, T. "Instability and decay of the primary structure of DNA" *Nature*, Apr. 22, 1993, pp. 709-715, vol. 362.

Fabre, A.-L. et al. "An efficient method for long-term room temperature storage of RNA" *European Journal of Human Genetics*, 2014 (published online Jul. 17, 2013), pp. 379-385, vol. 22.

Yang, T.-H. and Chang, P.-L. "Determination of RNA degradation by capillary electrophoresis with cyan light-emitted diode-induced fluorescence" *Journal of Chromatography A*, 2012, pp. 1-7.

Crommelin, D. J. A. et al. "Addressing the Cold Reality of mRNA Vaccine Stability" *Journal of Pharmaceutical Sciences*, 2021 (available online Dec. 13, 2020), pp. 997-1001, vol. 110.

Huang, C. et al. "Understanding Compression-Induced Amorphization of Crystalline Posaconazole" *Mol. Pharmaceutics*, 2019, pp. 825-833, vol. 16.

Bechard, S. R. et al. "Infrared Imaging of Pharmaceutical Materials Undergoing Compaction" *Pharmaceutical Research*, 1992, pp. 521-528, vol. 9, No. 4.

Felipe, A. V. et al. "RNA Interference: a Promising Therapy for Gastric Cancer" *Asian Pacific Journal of Cancer Prevention*, 2014, pp. 5509-5515, vol. 15, No. 14.

Liu, J. et al. "Inhibition of CXCR4 by MicroRNA-1192 Reduces the Activation of Th17 Cells and Expression of Inflammation Factors in a Mouse Model of Vulvovaginal Candidiasis" *Cell Physiology and Biochemistry*, published online Oct. 23, 2018, pp. 893-910, vol. 50.

Scarborough, R. J. et al. "RNA Interference Therapies for an HIV-1 Functional Cure" *Viruses*, Dec. 27, 2017, pp. 1-19, vol. 10, No. 8.

Blenke, E. O. et al. "The Storage and In-Use Stability of mRNA Vaccines and Therapeutics: Not A Cold Case" *Journal of Pharmaceutical Sciences*, 2023, pp. 386-403, vol. 112.

Dan, N. et al. "Structure and kinetics of lipid-nucleic acid complexes" *Advances in Colloid and Interface Science*, 2014, pp. 230-239, vol. 205.

Fenske, D. B. et al. "Liposomal Nanomedicines: An Emerging Field" *Toxicologic Pathology*, 2008, pp. 21-29, vol. 36, No. 1.

Hamoudi, M. C. et al. "Enhancement of siRNA lipid-based vector stability and siRNA integrity in human serum with addition of anionic polymer adjuvant" *Journal of Drug Delivery Science and Technology*, available online Jan. 15, 2015, pp. 1-9, vol. 26.

Van Winden, E. C. A. "Freeze-Drying of Liposomes: Theory and Practice" *Methods in Enzymology*, 2003, pp. 99-110, vol. 367.

Cortesi, R. et al. "Effect of DNA Complexation and Freeze-Drying on the Physicochemical Characteristics of Cationic Liposomes" *Antisense & Nucleic Acid Drug Development*, 2000, pp. 205-215, vol. 10.

Aso, Y. et al. "Effect of Freezing Rate on Physical Stability of Lyophilized Cationic Liposomes" *Chem. Pharm. Bull.*, Mar. 2005, pp. 301-304, vol. 53, No. 3.

Yadava, P. et al. "Effect of Lyophilization and Freeze-thawing on the Stability of siRNA-liposome Complexes" *AAPS PharmSciTech*, Jun. 2008, pp. 335-341, vol. 9, No. 2.

Bauer, K. H. et al. "Pharmazeutische Technologie", Wissenschaftliche Verlagsgesellschaft mbH, Stuttgart, 9th edition, 2012, Chapter 14.4, Tabletten, pp. 493-516.

Ritschel, W. A. et al. "Die Tablette", Editio Cantor Verlag, $2^{nd}$ edition, 2002, Chapter 5.6, Preßdruck, pp. 1-8.

Raoof, A. A. et al. "Effect of sodium caprate on the intestinal absorption of two modified antisense oligonucleotides in pigs" *European Journal of Pharmaceutical Sciences*, 2002, pp. 131-138, vol. 17.

* cited by examiner

NUCLEIC ACID VECTOR TABLETS

CROSS-REFERENCE TO RELATED APPLICATION

This application is the U.S. national stage application of International Patent Application No. PCT/EP2018/062141, filed May 9, 2018.

FIELD OF THE INVENTION

The invention relates to a process for the manufacture of a tablet comprising a nucleic acid vector.

TECHNOLOGICAL BACKGROUND OF THE INVENTION

Gene therapy uses nucleic acids (particularly DNA or RNA) to treat or prevent diseases. Depending on the pathology, the nucleic acid is administered to regulate, repair, replace, add or delete a genetic sequence. The therapeutic, prophylactic or diagnostic effect depends directly on the nucleic acid sequence or the product of the gene expression of that sequence. Therapeutic nucleic acids include, for example, antisense oligonucleotides, siRNAs and shRNAs. In particular, small interfering RNAs, or siRNAs, coupled with vectors, constitute active substances with high therapeutic potential due to their ability to specifically suppress the expression of pathological proteins. Therapeutic nucleic acids can be injected directly into the cells as bare nucleic acid, but they are most often transported into the patient's cells using a nucleic acid vector. Nucleic acid vectors can be viral vectors, or synthetic vectors based on polymeric or lipidic systems.

At present, nucleic acid vectors are in the form of colloidal suspensions administered mainly parenterally. This type of formulation and the route of administration impose strong constraints such as the size of the vectors administered or the obtaining of sterile preparations. These constraints are an obstacle to the development of nucleic acid vectors as new drug candidates.

There is therefore a need for new formulations of nucleic acid vectors to avoid the above-mentioned constraints while maintaining the biological activity of therapeutic nucleic acids.

SUMMARY OF THE INVENTION

According to a first aspect, the invention relates to a process for the manufacture of a tablet comprising a complex between:
(i) a nucleic acid; and
(ii) a lipid particle comprising a cationic lipid, the lipid particle being preferably a liposome or a micelle, preferably a liposome; said process comprising the following steps:
a) drying, in particular by freeze-drying, an aqueous mixture comprising:
  a complex between (i) a nucleic acid and (ii) a lipid particle comprising a cationic lipid, the lipid particle being preferably a liposome or a micelle, preferably a liposome;
  one or more excipient(s) suitable for drying, in particular for freeze-drying;
b) mixing one or more compression excipient(s) with the dry mixture obtained in step a); and
c) compressing the mixture obtained in step b).

In a particular embodiment, said cationic lipid is selected from lipopolyamines, quaternary ammoniums, and lipids having a cationic head of the guanidine or imidazole type, preferably the cationic lipid is selected from Di-Myristylaminopropylaminopropyl (DMAPAP), N-[1-(2,3-dioleyloxy)propyl]-N,N,N-trimethylammonium chloride (DOTMA), [1,2-bis(oleoyloxy)-3-(trimethylammonio)propane] (DOTAP), 3[N—(N',N'-dimethylaminoethane)-carbamoyl]cholesterol (DCChol) and dioctadecylamidoglycylspermine (DOGS), preferably Di-Myristylaminopropylaminopropyl (DMAPAP). Said cationic lipid may optionally be mixed with a neutral lipid, in particular selected from 1,2-dioleoyl-sn-glycero-3-phosphoethanolamine (DOPE), cholesterol, dioleoyl-sn-glycero-3-phosphocholine (DOPC), dipalmitoyl-sn-glycero-3-phosphocholine (DPPC) and N'-(rac-1-[11-(F-octyl)undec-10-enyl]-2-(hexadecyl)glycero-3-phosphoethanoyl)-sperminecarboxamide), preferably the neutral lipid is 1,2-dioleoyl-sn-glycero-3-phosphoethanolamine (DOPE). In particular, the mixture between the cationic lipid and the neutral lipid may include between 50 and 99 mol % of cationic lipid in the mixture, preferably about 50 mol %, and between 1 and 50 mol % of neutral lipid in the mixture, preferably about 50 mol %.

According to a particular embodiment, the complex comprises a therapeutic nucleic acid, particularly an siRNA, an miRNA, an shRNA, a plasmid, or a mRNA. According to a particular embodiment, the charge ratio (+/−) between the positive charges of the cationic lipid and the negative charges of the nucleic acid is between 0.5 and 10, preferably between 4 and 10, preferably about 8.

According to the process of the invention, the excipient(s) suitable for drying, in particular freeze-drying, may be protective agents (cryoprotectants or lyoprotectants) and/or fillers, in particular selected from trehalose, mannitol, sucrose, sorbitol, lactose, glucose, glycerol, glycine, alanine, lysine, polyethylene glycol, polyvinyl pyrrolidone and dextran, optionally in mixture. In particular, the excipient suitable for freeze-drying is trehalose, in particular in a proportion of between 10 and 100 mass % of the excipient(s) suitable for freeze-drying, optionally mixed with another excipient suitable for freeze-drying, preferably mannitol, in particular in a proportion of between 0 and 90 mass % of the excipient(s) suitable for freeze-drying.

According to the process of the invention, the compression excipient(s) protect the complex between the nucleic acid and the lipid particle comprising the cationic lipid during the compression step c), said compression excipients being in particular a lubricant (for example magnesium stearate, stearic acid and talc, preferably magnesium stearate), optionally mixed with another compression excipient, preferably a diluent (for example lactose, starch, calcium phosphate and derivatives thereof and cellulose and derivatives thereof, preferably lactose). In particular, the lubricant can represent 0.25 to 5 mass % of the finished tablet, preferably 0.5%.

In a particular embodiment, the process according to the invention comprises a compression step (step c) performed at a pressure between 10 and 400 MPa, preferably between 50 and 250 MPa.

According to another aspect, the invention relates to a tablet obtainable according to the process described above. The tablet of the invention may comprise:
  a complex between a nucleic acid and a liposome or a micelle comprising a cationic lipid;
  one or more suitable freeze-drying excipients to protect said complex during the freeze-drying step a) and/or to obtain a freeze-dried product of a texture suitable for the compression step, preferably trehalose and mannitol;

one or more suitable compression excipients to protect said complex during the compression step c) and to preserve the biological activity of the complex.

According to a particular embodiment, the tablet of the invention is intended for oral, vaginal, rectal, sublingual or transmucosal administration, preferably by the oral route.

The present invention also relates to the tablet described above for use in the treatment of gastrointestinal tract or vaginal disorders.

FIGURE LEGENDS

FIG. 6: SAXS profile of suspended siRNA lipoplexes. The first curve corresponds to samples that have undergone (A) freeze-drying, then (B) compression (see legend of FIG. 4), then resuspension by adding water. A second curve corresponds to the suspended sample that has not been freeze-dried or compressed but supplemented with the same amount of (A) trehalose/mannitol as the freeze-dried resuspended sample or (B) trehalose/mannitol/lactose as the resuspended compressed sample. Peak analysis identifies a single phase in the trace corresponding to the second curve, of cubic type ($C_1$, (A) $q=0.094$ $nm^{-1}$; (B) $q=0.096$ $nm^{-1}$), a cubic phase in the trace of the first curve in (A) ($C_1$, $q=0.093$ $nm^{-1}$) and two phases in the trace of the first curve in (B), a cubic ($C_1$, $q=0.086$ $nm^{-1}$) and a lamellar ($L_1$, $q=0.101$ $nm^{-1}$).

DETAILED DESCRIPTION OF THE INVENTION

The inventors propose forming nucleic acid vectors in tablet form for oral, vaginal, rectal, sublingual or transmucosal administration. The "tablet" form allows easy administration, while avoiding the formulation and administration constraints mentioned above. In addition, the tablet allows numerous formulation options to control or modulate the release of nucleic acid vectors based on the therapeutic targets. The "tablet" form also represents a breakthrough for the stability of nucleic acid vectors. In particular, it makes it possible to avoid their preparation just before use. In addition, the "tablet" form improves both patient comfort and compliance with treatments.

Before the implementation of the present invention, no nucleic acid vector tablets were available or even conceivable, as the skilled person fears a loss of nucleic acid activity during the steps necessary to form a tablet. However, against this prejudice, the inventors propose innovative means of producing nucleic acid vector tablets.

The invention relates to a process for the manufacture of a tablet comprising at least one nucleic acid vector. More particularly, the proposed invention makes it possible to formulate nucleic acid vectors in a "tablet" form, while maintaining their therapeutic properties despite the mechanical stresses associated with this forming operation.

Definitions

"Tablet" refers to any homogeneous solid formulation without a specific shape or size, obtained from compressed powder, wherein the powder may or may not be agglomerated.

"Nucleic acid vector" (otherwise referred to as "complex", below) refers to any structure known to be suited to vectorize a nucleic acid; in particular, these terms refer to a complex between (i) a nucleic acid and (ii) a lipid particle comprising a cationic lipid, the lipid particle being preferably a liposome or a micelle, preferably a liposome.

"Lipoplex" refers to a complex between (i) a nucleic acid and (ii) a liposome comprising a cationic lipid.

"Cationic lipid" refers to a lipid with a positive overall charge. A cationic lipid comprises a cationic polar head and one or more hydrophobic chain(s).

"Neutral lipid" refers to a lipid with a neutral overall charge, more particularly a zwitterionic lipid.

"Micelle" refers to a spheroidal aggregate of amphiphilic molecules with a hydrophilic polar head and a hydrophobic chain.

"Liposome" refers to an artificial vesicle formed by concentric lipid bilayers, trapping aqueous compartments between them.

For example, the nucleic acid vector may be selected from liposomes, lipids, for example cationic lipids, anionic lipids, amphoteric lipids or uncharged lipids, cationic polymers, polymers, hydrogels, micro or nanocapsules (biodegradable), microspheres (optionally bioadhesive), cyclodextrins, protein vectors, or any combination thereof. Preferably, the vector may be selected from lipid-based delivery systems, polyimine-based delivery systems, dendrimers, poly(lactide-co-glycolide) (PLGA) particles, systems described in WO15023775, and similar systems.

"About" means the value + or −10%, preferably + or −5% thereof. For example, about 50 means 45 to 55, and preferably 47.5 to 52.5.

Preparation of the Nucleic Acid Vector

The nucleic acid may in particular be deoxyribonucleic acid (DNA) or ribonucleic acid (RNA), of any size, single or double stranded, linear or circular, chemically unmodified or modified (such as phosphorothioate, phosphoroamidate and/or 2'-O-methyl forms). The size of the nucleic acid can vary widely, for example from 10 base pairs to several tens of thousands of base pairs. For example, the size of the nucleic acid can reach about 10,000 base pairs or more in the case of a plasmid, about 19-25 nucleotides in the case of a double-stranded siRNA or about 20-30 nucleotides in the case of a single-stranded microRNA. They can be natural, hybrid or synthetic sequences, of any origin (prokaryotic, eukaryotic, virus, parasite, plant, etc.). Preferably, the nucleic acid is a therapeutic nucleic acid, i.e. a nucleic acid that has a therapeutic effect through the regulation, repair, replacement, addition or deletion of a genetic sequence. Preferably, the nucleic acid can modulate the expression of a protein and may in particular be selected from antisense oligonucleotides, oligonucleotides for exon skipping, oligonucleotides for alternative splicing modification, interfering RNAs, messenger RNAs or plasmid DNA. Preferably, the nucleic acid is an interfering RNA. In the context of the invention, an "interfering RNA" is an RNA that inhibits gene expression. In particular, an interfering RNA is a small (notably between 20 and 25 base pairs, in particular between 21 and 23 base pairs) ribonucleic acid that interferes with a specific messenger RNA, leading to its degradation and inhibition of its translation into protein. For example, small interfering RNAs (siRNAs) and micro RNAs (miRNAs) are interfering RNAs.

In particular, the nucleic acid is selected from a plasmid, an siRNA, an miRNA, an mRNA and an shRNA, preferably the nucleic acid is an siRNA or an miRNA. Preferably, the nucleic acid is an siRNA.

The tablet manufactured according to the invention comprises one or more nucleic acid vector(s) (or complex(es)), as defined above. According to a particular embodiment, the tablet comprises a combination of several different nucleic acid vectors, particularly a combination of at least 2, at least 3, at least 4 or even at least 5 different nucleic acid vectors. According to another particular embodiment, the tablet comprises a combination of one or more nucleic acid vector(s) (or complex(es)) with at least one probiotic.

"Probiotic" refers to a living microorganism that, when administered in sufficient quantities, has positive health effects beyond traditional nutritional effects. Positive health effects include, for example, improved digestion or improved immune defenses.

According to the present invention, a complex is formed by electrostatic interactions between a negatively charged nucleic acid and a lipid particle comprising a cationic lipid.

Preferably, the lipid particle comprising a cationic lipid is a micelle or a liposome.

Even more preferably, the lipid particle is a liposome. According to this embodiment, the complex formed between the nucleic acid and the liposome is called a "lipoplex".

According to a particular embodiment, the invention relates to a process for the manufacture of a tablet comprising a complex between:
(i) a nucleic acid; and
(ii) a lipid particle comprising a cationic lipid, said lipid particle being preferably a liposome or a micelle, even more preferably a liposome.

According to a particular embodiment, the process of the invention may comprise, before the drying step described in detail below, a step of forming a complex between the nucleic acid and the lipid particle comprising a cationic lipid, the lipid particle being preferably a liposome or a micelle, preferably a liposome.

According to a particular embodiment, the nucleic acid can be pre-mixed with an anionic polymer prior to the step of forming the complex between the nucleic acid and the lipid particle. Said anionic polymer is an adjuvant to improve the structure of the complex between the nucleic acid and the lipid particle, and can thus increase the efficacy of said complex. The anionic polymer may be selected from anionic polysaccharides and anionic polypeptides, preferably the anionic polymer is selected from sodium alginate and sodium polyglutamate. According to a particular embodiment, the anionic polymer is an alginate, in particular sodium alginate. Thus, the manufacturing process according to the invention may also comprise a mixing step between the nucleic acid and an anionic polymer, prior to the step of forming the complex between the nucleic acid and the lipid particle.

In addition, the process according to the invention may comprise a prior step of forming the lipid particle comprising a cationic lipid, the lipid particle being preferably a liposome or a micelle, preferably a liposome.

Preferably, the cationic lipid is selected from cationic lipids capable of forming a particle by combining hydrophobic chains of several lipids. The cationic lipid according to the invention may be selected from lipopolyamines, quaternary ammoniums, and lipids having a cationic head of the guanidine or imidazole type. Preferably, the cationic lipid is selected from Di-Myristylaminopropylaminopropyl (or DMAPAP), N-[1-(2,3-dioleyloxy)propyl]-N,N,N-trimethylammonium chloride (or DOTMA), 1,2-bis(oleoyloxy)-3-(trimethylammonio)propane] (or DOTAP), 3β[N—(N',N'-dimethylaminoethane)-carbamoyl]cholesterol (DCChol), and dioctadecylamidoglycylspermine (or DOGS). Preferably, the cationic lipid is Di-Myristylaminopropylaminopropyl (or DMAPAP).

According to a particular embodiment, the cationic lipid is mixed with a neutral lipid. Preferably, the neutral lipid is selected from 1,2-dioleoyl-sn-glycero-3-phosphoethanolamine (DOPE), cholesterol, dioleoyl-sn-glycero-3-phosphocholine (DOPC), dipalmitoyl-sn-glycero-3-phosphocholine (DPPC) and N'-(rac-1-[11-(F-octyl)undec-10-enyl]-2-(hexadecyl)glycero-3-phosphoethanoyl)-sperminecarboxamide). Preferably, the neutral lipid is 1,2-dioleoyl-sn-glycero-3-phosphoethanolamine (DOPE).

Thus, the tablet according to the invention may comprise a complex between (i) a nucleic acid and (ii) a lipid particle comprising a cationic lipid optionally mixed with a neutral lipid.

According to a preferred embodiment, the tablet according to the invention comprises a complex between (i) a nucleic acid and (ii) a lipid particle comprising a mixture between a cationic lipid and a neutral lipid. Preferably, the lipid particle is a micelle or a liposome, preferably a liposome.

The mixture between the cationic lipid and the neutral lipid includes in particular a defined proportion of cationic and neutral lipids. Preferably, the proportion of cationic lipid is between 50 and 99 mol % lipid in the mixture. In particular, the proportion of cationic lipid can be about 50 mol %, about 60 mol %, about 70 mol %, about 80 mol % or about 90 mol % lipid in the mixture. Preferably, the proportion of cationic lipid is about 50 mol % lipid in the mixture.

Preferably, the proportion of neutral lipid is between 1 and 50 mol % lipid in the mixture. In particular, the proportion of neutral lipid can be about 10 mol %, about 20 mol %, about 30 mol %, about 40 mol % or about 50 mol % lipid in the mixture. Preferably, the neutral lipid proportion is about 50 mol % lipid in the mixture.

According to a preferred embodiment, the cationic lipid is mixed with the neutral lipid in a 1:1 equimolar ratio.

The process according to the invention may comprise a mixing step between the cationic lipid and the neutral lipid, prior to the step of forming the lipid particle, the lipid particle being then used during the step of forming the complex with the nucleic acid.

According to a particular embodiment, the mixture between a cationic lipid and a neutral lipid is a mixture between DMAPAP and DOPE.

According to a particular embodiment, the nucleic acid of the invention is mixed with the lipid particle of the invention according to a defined charge ratio. The "charge ratio" corresponds to the +/− ratio between the number of positive charges of the cationic lipid and the number of negative charges of the nucleic acid. This charge ratio can influence the efficacy of the formed complex by influencing the physicochemical properties (for example size or surface charge). Said charge ratio can vary and be adapted by the skilled person, depending on the lipid and nucleic acid selected and the desired application (targeted organ or cell type). Preferably, the +/− charge ratio is between 0.5 and 10, for example about 1, 2, 3, 4, 5, 6, 7, 8, 9 or 10. Preferably, the +/− charge ratio is between 4 and 10, for example about 4, 5, 6, 7, 8, 9 or 10. Even more preferably, the charge ratio is about 8.

According to a particular embodiment, the mixture between the nucleic acid and the lipid particle is an aqueous mixture. Thus, the process according to the invention may comprise a step of preparing an aqueous mixture between the nucleic acid and the lipid particle comprising a cationic lipid.

Preferably, the aqueous mixture between the nucleic acid and the lipid particle is carried out in a buffer solution. In particular, the pH of said buffer solution is about 4 to 8. Preferably, the buffer solution chosen is a solution comprising NaCl. Said buffer solution may include a NaCl concentration of about 150 mM. For example, the skilled person may use a HEPES or Opti-MEM type buffer solution, or a solution comprising glucose.

Thus, according to a particular embodiment, the process for the manufacture of a tablet according to the invention may comprise:
  a step of forming the lipid particle, preferably the liposome, in a buffer solution; and/or
  a step of preparing the nucleic acid in a buffer solution; and/or
  a step of mixing the nucleic acid and the lipid particle in a buffer solution.

According to a particular embodiment, the mixing time between the nucleic acid and the lipid particle, preferably a liposome, is between 10 seconds and several days, for example between 10 seconds and 10 hours, particularly between 5 minutes and 5 hours, in particular between 10 minutes and 1 hour. Preferably, the mixing time is greater than or equal to 30 minutes, particularly equal to about 30 minutes. Mixing can be carried out over a wide temperature range. However, according to a preferred embodiment, the mixing is carried out at a temperature between 10° C. and 30° C., in particular between 15° C. and 25° C.

After the complex has been formed, it may be subjected directly to the following steps of the process according to the invention, or preserved, in particular for at least 1 day, before said following steps.

"Tablet" Formulation

The process according to the invention comprises a phase of tablet formulation from the aqueous mixture comprising the nucleic acid and the lipid particle as described above. The inventors of the present application have succeeded in putting nucleic acid vectors (or complexes) in "tablet" form for potential oral, vaginal, rectal, sublingual or transmucosal administration, while maintaining the biological properties of said nucleic acid vectors.

More particularly, the process according to the invention comprises the steps of:
  drying the aqueous mixture comprising a complex as defined above; and
  compressing the dry mixture thus obtained.

Preferably, the process according to the invention comprises the following steps:
  a) drying an aqueous mixture comprising:
    the complex as defined above; and
    one or more excipient(s) suitable for drying
  b) mixing one or more compression excipient(s) with the dry mixture obtained in step a); and
  c) compressing the mixture obtained in step b).

Drying Step a):

Drying refers to any dehydration process capable of removing water contained in a substance or body. For example, drying can be achieved by spray drying, convective drying or freeze-drying. According to a preferred embodiment, drying is carried out by freeze-drying. According to this embodiment, the excipient(s) suitable for drying are excipients suitable for freeze-drying. Freeze-drying is a low-temperature, vacuum drying process that removes water from a previously frozen product by sublimation.

According to a preferred embodiment, the drying step a) is freeze-drying. According to a particular embodiment, the freeze-drying process implemented comprises the following steps:
  freezing the aqueous mixture comprising a complex as defined above and one or more excipient(s) suitable for freeze-drying;
  primary drying (or sublimation); and
  secondary drying.

Preferably, the process according to the invention comprises, prior to the drying step, a step of mixing the complex as defined above with the excipient(s) suitable for drying.

The excipient(s) suitable for drying are excipients capable of preserving the structure of nucleic acid vectors during the drying step, thus preserving the biological activity of the nucleic acid. The excipient(s) suitable for drying also provide a dry mixture suitable for the compression step. In particular, the excipient(s) make it possible to obtain a dry product whose texture (influenced by residual moisture) is suitable for the compression step. The excipient(s) also make it possible to obtain a dry product whose mass and/or mechanical strength are suitable for the compression step, said excipients making it possible, for example, to avoid a collapse of the structure of the dry product. Preferably, said excipient(s) suitable for drying, preferably for freeze-drying, facilitates the grinding and homogeneous mixing of the dry product obtained with the compression excipient(s). The optimization of parameters such as texture, mass and/or mechanical strength of the dry product by choosing the nature and quantity of excipients suitable for drying is traditionally carried out by the skilled person, in particular according to the physicochemical characteristics of each of the excipients (existence of eutectics, glass transition temperatures, etc.).

According to the preferred embodiment of the invention, using freeze-drying in step a), the excipient(s) suitable for drying are suitable for freeze-drying. Thus, the excipient(s) suitable for freeze-drying protect the complex during the freeze-drying step and/or make it possible to obtain a freeze-dried product of a texture suitable for the compression step.

According to a particular embodiment, the excipient(s) suitable for freeze-drying are protective agents (cryoprotectants or lyoprotectants) and/or fillers (or ballasts). Cryoprotective excipients are excipients that protect the structures of nucleic acid vectors during the freezing step. Lyoprotective excipients are excipients that protect the structures of nucleic acid vectors during the dehydration step. During freeze-drying, these agents substitute water molecules to interact with the polar heads of phospholipids (water replacement hypothesis) and form a vitreous matrix that helps to maintain the structure of lipoplexes (vitrification hypothesis). Fillers (or ballasts) are excipients that maintain the structure and rigidity of the lyophilizate (as opposed to a collapsed state).

According to a specific embodiment, the excipient(s) suitable for freeze-drying are selected from trehalose, mannitol, sucrose, sorbitol, lactose, glucose, glycerol, glycine, alanine, lysine, polyethylene glycol, polyvinyl pyrrolidone (PVP) and dextran, optionally in mixture.

According to a particular embodiment, the excipient suitable for freeze-drying is trehalose, in a proportion of between 1 and 100 mass %, in particular between 10 and 100 mass %, based on the mass of excipient(s) suitable for freeze-drying. For example, the proportion of trehalose is about 10 mass %, about 20 mass %, about 30 mass %, about 40 mass %, about 50 mass %, about 60 mass %, about 70 mass %, about 80 mass %, about 90 mass % or about 100 mass % of the excipient(s) suitable for freeze-drying.

According to a particular embodiment, the excipient suitable for freeze-drying is mannitol, in a proportion of between 1 and 90 mass % of the excipient(s) suitable for freeze-drying. For example, the proportion of mannitol is about 0 mass %, about 10 mass %, about 20 mass %, about 30 mass %, about 40 mass %, about 50 mass %, about 60 mass %, about 70 mass %, about 80 mass % or about 90 mass % of the excipient(s) suitable for freeze-drying.

Preferably, the excipient suitable for freeze-drying is trehalose, optionally mixed with another excipient suitable for freeze-drying selected from mannitol, sucrose, sorbitol, lactose, glucose, glycerol, glycine, alanine, lysine, polyethylene glycol, polyvinyl pyrrolidone (PVP) and dextran, preferably mannitol.

According to a particular embodiment, trehalose is mixed with mannitol in defined proportions. In particular, the proportion of trehalose can be between 10 and 99 mass % of the trehalose/mannitol mixture. For example, the proportion of trehalose is about 10 mass %, about 20 mass %, about 30 mass %, about 40 mass %, about 50 mass %, about 60 mass %, about 70 mass %, about 80 mass % or about 90 mass % of the trehalose/mannitol mixture, preferably about 71 mass % of the trehalose/mannitol mixture.

According to a particular embodiment, the proportion of mannitol can be between 1 and 90 mass % of the trehalose/mannitol mixture. For example, the proportion of mannitol is about 10 mass %, about 20 mass %, about 30 mass %, about 40 mass %, about 50 mass %, about 60 mass %, about 70 mass %, about 80 mass % or about 90 mass % of the trehalose/mannitol mixture, preferably about 29 mass % of the trehalose/mannitol mixture.

According to a particular embodiment, the process according to the invention may comprise the following steps:
- preparing excipients suitable for drying, said excipients being preferably prepared in aqueous media;
- mixing the excipients suitable for drying with the complex defined above; and
- drying, in particular by freeze-drying, the mixture thus obtained.

According to a particular embodiment, the freezing step implemented during freeze-drying corresponds to the freezing of the mixture comprising the excipients suitable for drying and the complex defined above. Freezing is carried out in such a way as to preserve the biological activity of the nucleic acid vectors, preferably in such a way as to preserve the supramolecular assembly of the nucleic acid vectors. Freezing parameters are controlled to promote amorphization and/or to limit crystal growth of the components of the mixture.

Preferably, the freezing kinetics is fast, depending in particular on the freezing temperature. Preferably, the freezing rate is between $-40°$ C./min and $-0.5°$ C./min.

Preferably, in order to promote amorphization, freezing is carried out in liquid nitrogen, whose temperature is in particular of about $-190°$ C. Preferably, the freezing time in liquid nitrogen is between 1 minute and 24 hours, in particular between 1 minute and 1 hour, said freezing time being in particular about 10 minutes.

According to a particular embodiment, the parameters of the freeze-drying process make it possible to preserve the biological activity of said complexes. In particular, the operating parameters that control the freeze-drying cycle (ambient or shelf temperature, pressure in the drying chamber and cycle duration) are chosen appropriately to maintain the biological activity of the complexes, and can be adapted according to the volume of the aqueous mixture comprising said complexes (more particularly according to the volume of water to be sublimated).

According to a particular embodiment, the freeze-drying duration comprising primary and secondary drying is between 10 and 80 hours, preferentially between 15 and 72 hours, more preferentially between 20 and 48 hours, preferably around 30 hours. The freeze-drying time can be adapted by the skilled person according to the volume and the formulation of the aqueous mixture to be freeze-dried.

According to a particular embodiment, drying, in particular by freeze-drying, is carried out at atmospheric pressure.
Mixing Step b):

The process according to the invention may comprise a step to break the structure of the product obtained after drying. This step can be a step of light grinding (low energy) or of redispersion of the product. It can be carried out for example by using a vibration or calibration grid, or in a paddle mixer for example when mixing with the diluent.

Before compression, the dry mixture, optionally ground, is mixed with one or more compression excipient(s). "Compression excipient" means any excipient:
- to protect the complex between the nucleic acid and the lipid particle during the compression step c); and/or
- to reduce friction phenomena during the compression step c); and/or allowing a regular feeding of the matrix used for compression, the matrix delimiting the compartment where the powder is compressed; and/or to obtain a tablet of sufficient mass and adequate mechanical strength; and/or to control or delay the release of the nucleic acid vector; and/or allowing the tablet to be disintegrated.

According to a particular embodiment, the compression excipient(s) is/are selected from among the excipients used in granular mixtures for compression.

In a preferred embodiment, the compression excipient is a lubricant, optionally mixed with at least one other compression excipient well known to the skilled person, preferably a diluent.

"Lubricant" means any excipient that reduces the adhesion of the powder to the punch and die of the compression machine, and/or reduces friction between the particles and the die during compression and ejection of the tablet.

According to a particular embodiment, the lubricant represents 0.25 to 5 mass % of the finished tablet. Preferably, the lubricant represents about 0.5 mass % of the finished tablet. According to a preferred embodiment, the lubricant is selected from magnesium stearate, talc, sodium stearyl fumarate and stearic acid, optionally in mixture. Preferably, the lubricant is magnesium stearate.

"Diluent" means any excipient having a filling role when the amount of active ingredient and other excipients is insufficient to make a tablet of suitable size, thus allowing adjustment of the mass and dimensions of the tablet.

According to a preferred embodiment, the diluent is selected from lactose, starch and derivatives thereof, calcium phosphate and derivatives thereof, in particular dicalcium phosphate and cellulose and derivatives thereof, in particular microcrystalline cellulose, optionally in mixture. Preferably, the diluent is lactose.

The tablet may further contain pharmaceutical excipients well known to the skilled person such as flow agents, disintegrants, binders, excipients to control or delay the release of nucleic acid vectors, excipients that give the tablet mucoadhesive properties and their combination. For example, the tablet may contain one or more of the following excipients: sucrose, glucose, mannitol, trehalose and silica.

Preferably, the compression excipient(s) are dry excipients, preferably in powder form.

The process of the invention may comprise a step of mixing the different compression excipients prior to the mixing step with the dry mixture obtained after the drying step a).

Compression Step c):

The process according to the invention further comprises a step c) of compression of the mixture obtained at the end of step b). The compression step is carried out under conditions that preserve the biological function of the nucleic acid vectors. In particular, the compression step is carried out in such a way as to preserve the therapeutic activity of nucleic acid vectors, for example the inhibition of the expression of a target gene, in the case of siRNA.

Mechanical stresses applied during the compression step can be controlled and monitored. More specifically, the pressure applied to the mixture comprising the nucleic acid vectors according to the invention is controlled and monitored during the compression step. Preferably, the compression of step c) is performed at a pressure between 10 and 400 MPa, preferably between 50 and 250 MPa.

According to a preferred embodiment, the compression of step c) is carried out by means of a tablet press, for example a rotary press or an alternative press.

In a particular embodiment, a step of wet granulation or of dry granulation is carried out before the compression step c). The "wet granulation" or "dry granulation" steps consist in increasing the size of the particles in order to obtain agglomerates, in order to facilitate compression. More particularly, the wet granulation step comprises the addition of a binding agent to obtain granules in the form of agglomerates which are then dried and optionally screened before the compression step. Dry granulation consists in strongly compressing the particles to obtain an agglomerate before grinding them to form grains which are optionally calibrated before the final forming step by compression.

According to a preferred embodiment, the compression step c) is a direct compression, direct compression not requiring a prior granulation step. According to this embodiment, the dry mixture obtained at the end of the drying step (step a)), optionally mixed with compression excipients (step b)), has properties suitable for direct compression.

In a particular embodiment, the process according to the invention comprises, after the compression step, a step of film-coating (or coating) the obtained tablet. The advantage of this step is the production of a tablet that is better protected, whose stability is improved, and/or whose release kinetics is adapted. The nature of the film-coating and/or coating agents and the process used to carry out this step are well known to the skilled formulator.

According to a second aspect, the invention relates to a tablet obtainable by the process described above.

In particular, the invention relates to a tablet comprising:
one or more nucleic acid vector(s) (or complex(s)) as described above;
one or more excipient(s) suitable for drying;
one or more compression excipient(s).

In particular, the tablet of the invention may comprise:
a complex between a nucleic acid and a liposome or a micelle comprising a cationic lipid;
one or more suitable freeze-drying excipients to protect said complex during the freeze-drying step a) and/or to obtain a freeze-dried product of a texture suitable for the compression step, preferably trehalose and mannitol;
one or more suitable compression excipients to protect said complex during the compression step c) and to preserve the biological activity of the complex.

In particular, the finished tablet contains 1 µg to 1 mg of nucleic acid, preferably about 10 µg.

The mass of cationic lipid in the finished tablet can be between 18.7 µg and 18.7 mg, preferably about 170 µg.

The mass of neutral lipid in the finished tablet can be between 16.5 µg and 16.5 mg, preferably about 150 µg.

The mass of polymer in the finished tablet can be between 1 µg and 1 mg, preferably about 10 µg.

The mass of excipients suitable for drying may be included in the finished tablet between 36 mg and 720 mg, preferably about 126 mg. In particular, the mass of trehalose in the finished tablet may be between 3.6 mg and 720 mg, preferably about 90 mg. In particular, the mass of mannitol in the finished tablet may be between 0 mg and 648 mg, preferably about 36 mg.

The proportion of excipients suitable for compression can be between 0.25 and 95 mass % of the finished tablet. In particular, the proportion of lubricant, preferably magnesium stearate, may be between 0.25 and 5 mass % of the finished tablet, preferably about 0.5 mass %. In particular, the proportion of other compression excipients may be between 0 and 94.75 mass % of the finished tablet.

According to a particular embodiment, the tablet according to the invention comprises:
- a complex between a nucleic acid and a liposome or a micelle comprising DMAPAP and DOPE, the complex further comprising alginate, in particular sodium alginate;
- trehalose and mannitol; and
- lactose.

According to a variant of this embodiment, the tablet thus composed has, after resuspension in water, a synchrotron radiation small-angle X-ray scattering (SAXS) profile comprising a cubic phase and a lamellar phase, and optionally a liquid crystal phase. The SAXS profile can be determined according to the protocol presented in the examples. The SAXS profile of the tablet according to the invention after resuspension in water shows peaks at $q=0.086$ nm$^{-1}$ and $q=0.101$ nm$^{-1}$. According to a particular embodiment, the lamellar phase is the majority compared with the cubic phase.

According to a particular embodiment, the tablet according to the invention is intended for oral, vaginal, rectal, sublingual or transmucosal administration. Preferably, the tablet according to the invention is intended for oral administration.

According to another aspect, the present invention relates to the tablet of the invention for use in the treatment of local, locoregional or systemic pathologies. Preferably, the tablet according to the invention is used in the treatment of diseases of the gastrointestinal tract. For example, diseases of the gastrointestinal tract may be Crohn's disease (nucleic acid being for example an siRNA inhibiting inflammatory proteins such as TNF-α), ulcerative colitis (the nucleic acid being for example an anti-ICAM-1 oligonucleotide, an IL-10 encoding plasmid or an anti-TNF-α siRNA), or gastric cancer (the nucleic acid being for example an siRNA or an anti-Her2 oligonucleotide). The tablet according to the invention can also be used in the treatment of vaginal pathologies, particularly vulvovaginal candidiasis or HSV, HPV or HIV infection (via the administration of antiviral siRNAs for example).

In addition, the tablet can be used in the treatment of conditions such as spinal muscular atrophy (the nucleic acid being for example the antisense oligonucleotide Nusinersen), familial hypercholesterolemia (nucleic acid being for example the antisense oligonucleotide Mipomersen), Duchenne myopathy, or age-related macular degeneration (nucleic acid being for example the aptamer Macugen).

The tablet according to the invention is stable, i.e. it substantially retains its biological activity, preferably for up to 2 weeks, 1 month, 3 months, 1 year, at room temperature (between the formulation of the tablet and administration).

EXAMPLES

Example 1: Preparation of the Tablet

1. Lipoplex Formation

The first step consists of the formation of the lipoplex, i.e. the complex between the nucleic acid and the liposome. The nucleic acid used in this example is a luciferase-specific siRNA. The liposome used here includes a cationic lipid (DMAPAP) and a neutral lipid (DOPE). The formation of lipoplexes was carried out using the following components:

| | |
|---|---|
| luciferase siRNA or control siRNA | 1.33 µg/µL |
| liposome (DMAPAP, DOPE) | 20 mM |
| polymer (sodium alginate) | 1.5 µg/µL |
| NaCl | 150 mM in Milli-Q water |

The siRNA, liposome and polymer preparations were vortexed.

The liposome was mixed with the NaCl solution to obtain a final volume of 200 µL (10.7 µL of liposome with 189 µL of NaCl solution).

Additionally, the siRNA was mixed with the polymer in a NaCl solution to obtain a final volume of 200 µL (7.5 µL of siRNA+6.5 µL of polymer+186 µL of NaCl solution). The resulting mixture therefore includes a ratio between siRNA and polymer of 1:1 by mass.

The two preparations obtained, each 200 µL, were mixed, vortexed and then left at room temperature for 30 min to allow the formation of the complex between the siRNA and the liposome.

The above components were mixed to form a lipoplex with a +/− charge ratio of 8.

2. Freeze-Drying

In this example, mannitol and trehalose were used as excipients suitable for freeze-drying. The previously obtained lipoplex suspension was transferred to a 50 mL centrifuge tube. A solution comprising 2.5% m/v trehalose and 1% m/v mannitol was prepared. 3.6 mL of this trehalose/mannitol solution was then added to the 400 µL of lipoplex suspension. The tube was then immersed in liquid nitrogen for 10 minutes.

Freeze-drying was performed on a freeze-dryer with a manifold equipped with 12 valves to which the frozen sample tubes are connected. Freeze-drying was carried out for 30 hours at a pressure in the freeze-drying chamber of less than 0.2 mbar (more particularly between 0.1 and 0.18 mbar). The energy required to compensate for the energy absorbed during sublimation is supplied by the ambient air (ambient temperature, more particularly between 20 and 25° C.).

Figure 1:
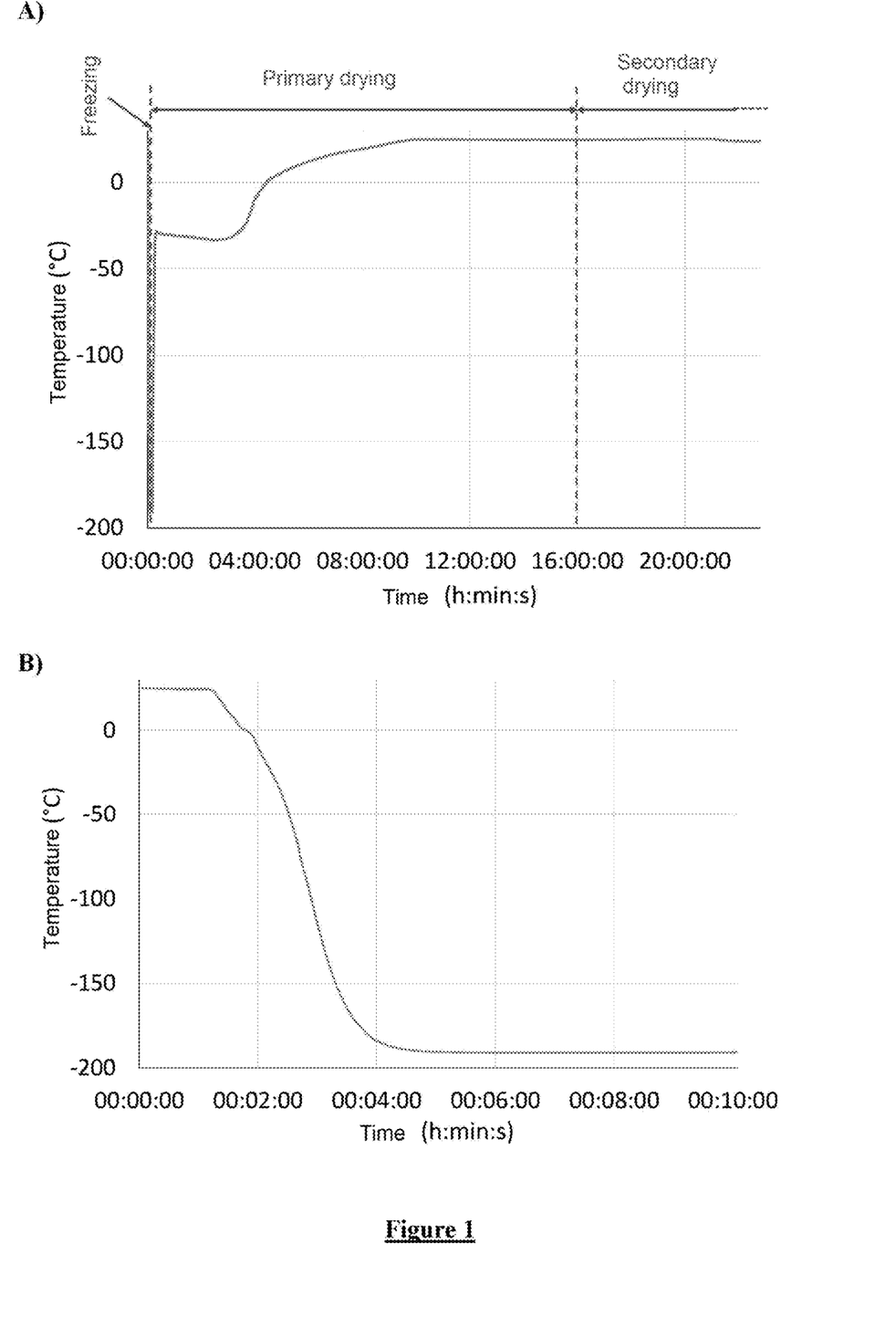
FIG. 1: Freeze-drying cycle: Representation of product temperature during the three stages of the cycle; (a) freezing, primary drying and beginning of secondary drying; (b) focus on freezing in liquid nitrogen.

Temperature sensors were placed in the samples to monitor the product temperature during the freezing (see FIG. 1b) and freeze-drying (see FIG. 1a) process.

3. Compression

In this example, magnesium stearate (lubricant) and lactose (diluent) were used as suitable excipients for compression.

The lyophilizate obtained previously was first reduced to powder by light grinding in a mortar. Then 36.2 mg of lactose and 0.8 mg of magnesium stearate were added to the mortar and mixed with the lyophilizate.

The compression was performed using a STYL'One Evolution compression simulator according to the following parameters:
- 6 mm diameter chamfered flat punches
- Compression cycle=cycle 1 compression (default cycle), speed 2%
- Force control
- Dosing (die filling height)=18 mm
- Manual filling
- Compression force=1.4 to 7.1 kN (50 to 250 MPa).

Example 2: Examples of Composition of Tablets Containing Lipoplexes

The following Table 1 is presented to illustrate the composition of tablets containing lipoplexes. The different components are expressed in mg.

TABLE 1

Examples of composition of tablets containing lipoplexes.

| | Tablet 1 | Tablet 2 | Tablet 3 |
|---|---|---|---|
| Nucleic acid | 0.01 mg | 0.10 mg | 0.01 mg |
| DMAPAP | 0.17 mg | 1.70 mg | 0.17 mg |
| DOPE | 0.15 mg | 1.50 mg | 0.15 mg |
| Alginate | 0.01 mg | 0.10 mg | 0.01 mg |
| Trehalose | 90.00 mg | 90.00 mg | 90.00 mg |
| Mannitol | 36.00 mg | 36.00 mg | 36.00 mg |
| Mg stearate | 0.75 mg | 0.75 mg | 2.25 mg |
| Lactose | 22.91 mg | 19.85 mg | 126.34 mg |

Example 3: Testing the Efficacy of the Tablet

The efficacy of the tablets is then evaluated on cells in culture expressing the luciferase gene. When these cells are exposed to vectors containing luciferase-specific siRNAs, the luciferase activity is inhibited. The test consists of transfecting mouse melanoma cells expressing luciferase (B16-Luc) and determining the residual luciferase activity in the cells 48 hours later. Relative to the activity of cells not treated or treated with vectors containing control siRNAs (without inhibitory effect), this measure makes it possible to obtain the percentage of inhibition induced by the siRNA vector studied.

To evaluate the maintenance of this activity after compression, the tablets are solubilized before being brought into contact with the cells to be transfected. Lyophilizates (obtained before the compression step) were also rehydrated to analyse the efficacy of the dry mixture before compression.

The test therefore consisted in treating B16-Luc cells with:
- A negative control: i.e. lipoplexes containing a control siRNA (whose sequence has been chosen so that it does not inhibit any protein target), resuspended from a compressed form;
- A positive transfection control: i.e. suspended lipoplexes (not freeze-dried, not compressed);
- A rehydrated lyophilizate; or
- A rehydrated tablet.

More precisely, the suspended lipoplexes (corresponding to the positive transfection control) were prepared as described above and then mixed with culture medium. The culture medium is complete medium (DMEM+Glutamax+ foetal calf serum+penicillin/streptomycin) supplemented with geneticin (G418).

The lyophilizate and the tablet were prepared as described above, then dissolved in distilled or Milli-Q water and mixed with culture medium.

The operation takes place over 4 days (day 0, day 1, day 2 and day 3):
- On day 0, the cells are prepared on a 24-well plate (40,000 cells/well).
- On day 1, the cell culture medium is replaced by 1 mL of transfection medium (so as to add 0.5 µg of siRNA per well). The transfection medium is the medium comprising the negative control, the positive transfection control, the lyophilizate or the tablet.
- On day 2, the transfection medium is replaced by culture medium (complete medium+G418).
- On day 3, the cells are lysed and luciferase activity is measured.

The test is performed in triplicate (3 repetitions per condition).

Results:

Test of the Efficacy of the Tablet

Figure 2:
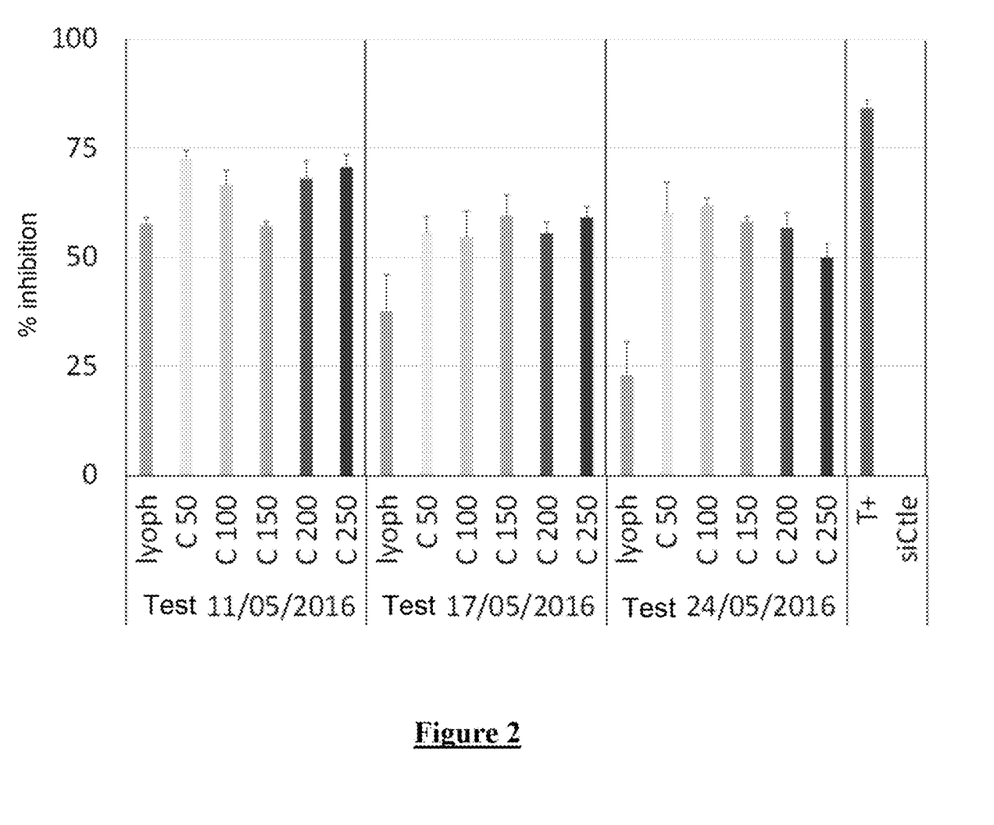
FIG. 2: Efficacy of lyophilizates (=lyoph) and tablets containing lipoplexes as a function of the compressive stress applied during the compression process (CX with X=50, 100, 150, 200 or 250 MPa): Transfection on B16-Luc cells for 48 h, in triplicate, 0.5 µg luciferase siRNA per well. Measure of luciferase and expression of the percentage of inhibition compared to non-transfected cells. Positive control (T+): cells transfected with lipoplexes prepared just before use (not freeze-dried and not compressed), negative control (siCtle): cells transfected with lipoplexes containing a control siRNA, resuspended from a tablet.

Transfection tests on cells have shown a good efficacy of tablets containing lipoplexes (efficacy expressed by the percentage of inhibition of the tablets compared with non-transfected cells). In addition, over the entire range of compressive stresses applied, no compressive stress effect was observed on the percentage of inhibition of the luciferase gene (FIG. 2).

Example 4: Supramolecular Structure

The small-angle X-ray scattering (SAXS) technique was used to identify the supramolecular structure of siRNA vectors, both on suspended particles and on dry forms, such as a lyophilizate or a tablet. The siRNAs used are control siRNAs, and each sample contains 100 micrograms of siRNA. This identification is made necessary by the fact that the structure of this type of particles is directly related to their efficacy in administering nucleic acid. Synchrotron radiation SAXS analysis is the only technology that provides access to this structure identification in various galenic forms, suspended in an aqueous medium or in a powder.

Figure 3:
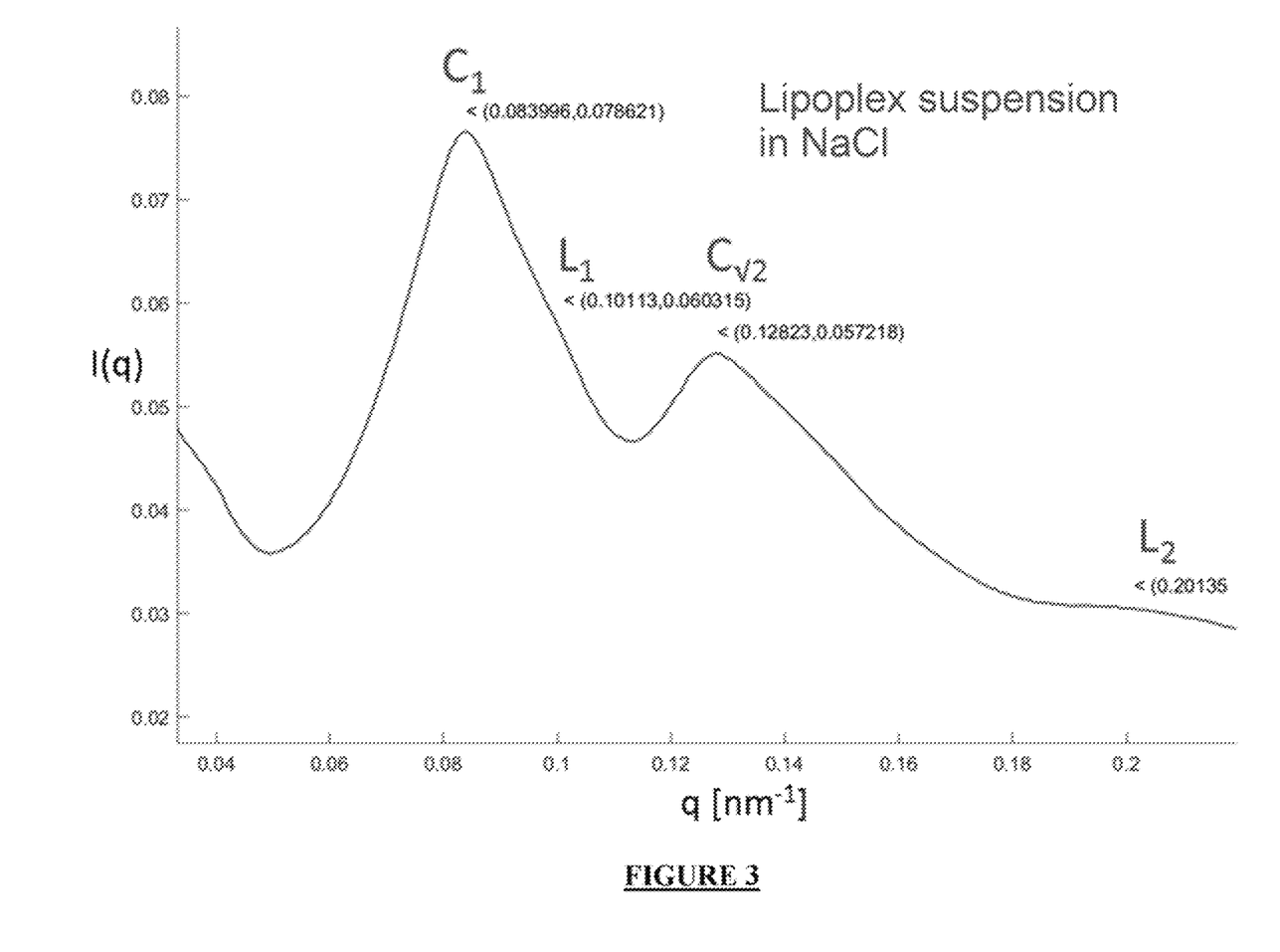
FIG. 3: SAXS profile of siRNA lipoplexes (DMAPAP/DOPE+Alginate), prepared at a +/− charge ratio of 8 in a 150 mM NaCl buffer. Peak analysis identifies two phases, a cubic major peak ($C_1$, $q=0.084$ $nm^{-1}$) and a minor lamellar peak ($L_1$, $q=0.101$ $nm^{-1}$).

First, the structure of siRNA lipoplexes (DMAPAP/DOPE+alginate) prepared at a +/− charge ratio of 8 was determined. The study conducted on lipoplexes suspended in a salt buffer (150 mM NaCl) showed that these lipoplexes were in the form of two coexisting structures, a lamellar phase and a cubic phase (FIG. 3).

Figure 4:
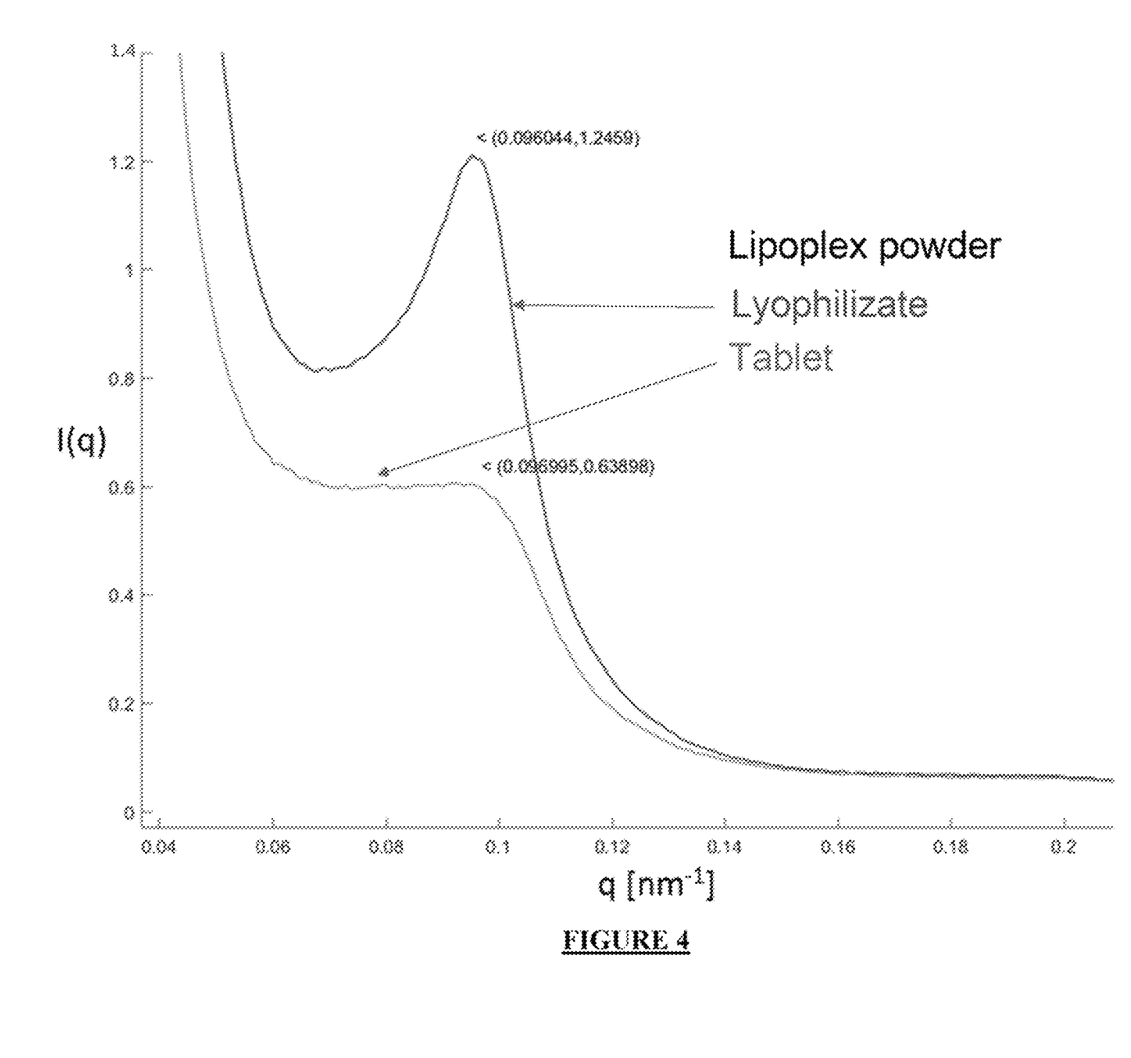
FIG. 4: SAXS profile of siRNA lipoplexes in dry, powder form, having undergone a freeze-drying step and then a compression step. The siRNA lipoplexes (DMAPAP/DOPE+Alginate), prepared at a +/− charge ratio of 8 in a 150 mM NaCl buffer, are supplemented with trehalose and maltose and then freeze-dried for 30 hours. The lyophilizate is weighed, supplemented with lactose and compressed. The SAXS analysis is performed on lyophilizate or tablet powder placed in a capillary. A single large peak ($q=0.096$ $nm^{-1}$) is detected.

We then studied the fate of this structure when the suspended vectors underwent a freeze-drying step, a necessary prerequisite before the compression step could be performed, and then after the compression step. FIG. 4 shows that a signal is detected for both types of samples (lyophilizate and tablet), with a single peak more or less wide at $q=0.096$ $nm^{-1}$. Its position, intermediate between the values of peaks $L_1$ and $C_1$ of the suspended lipoplex (FIG. 3), and its uniqueness do not make it possible to deduce the phase corresponding to this peak. The peak observed for the freeze-dried sample is more intense than that of the compressed sample, but the latter remains perfectly detectable.

Figure 5:
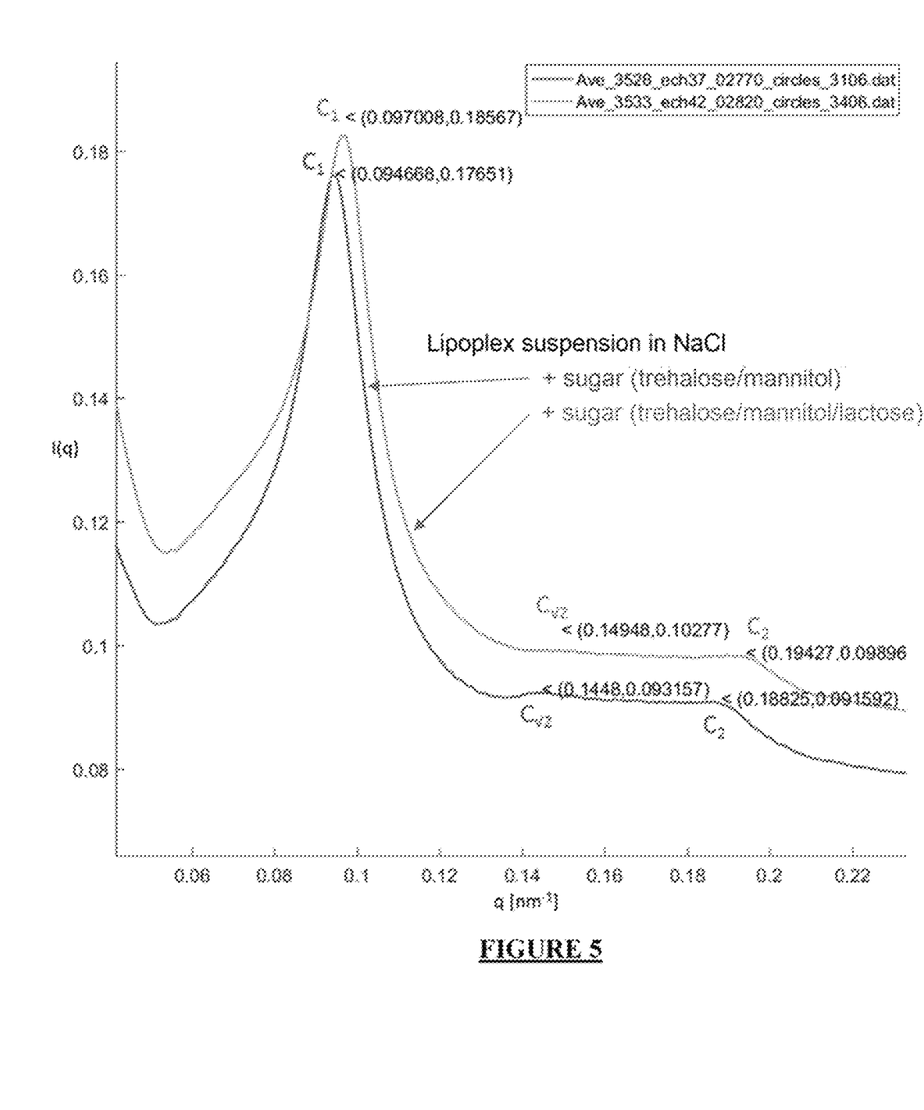
FIG. 5: SAXS profile of siRNA lipoplexes suspended in NaCl/sugar. Lipoplexes prepared as indicated in the legend of FIG. 3 are supplemented with a first Trehalose/Mannitol mixture or second Trehalose/Mannitol/Lactose mixture under the same conditions as the freeze-dried or compressed samples respectively. Peak analysis identifies a single cubic phase whose position of the first peak is slightly offset between the trace of the first mixture ($C_1$, $q=0.095$ $nm^{-1}$) and the trace of the second mixture ($C_1$, $q=0.097$ $nm^{-1}$).

The freeze-drying and compression steps require the addition of excipients. We therefore evaluated the signals obtained for lipoplexes diluted in a NaCl/excipients mixture under the same concentration conditions as the freeze-dried and compressed samples (FIG. 5). The profiles obtained indicate the presence of a single cubic phase, the first peak of which is slightly offset between the "lyophilizate" and "tablet" conditions. The position of this peak is close to the peak detected during the powder analysis, which could indicate that the phase present in the dry forms is a cubic phase. The peak corresponding to the lamellar phase is no longer detectable, either in dry forms or in suspensions, in the presence of excipients.

Figure 6:
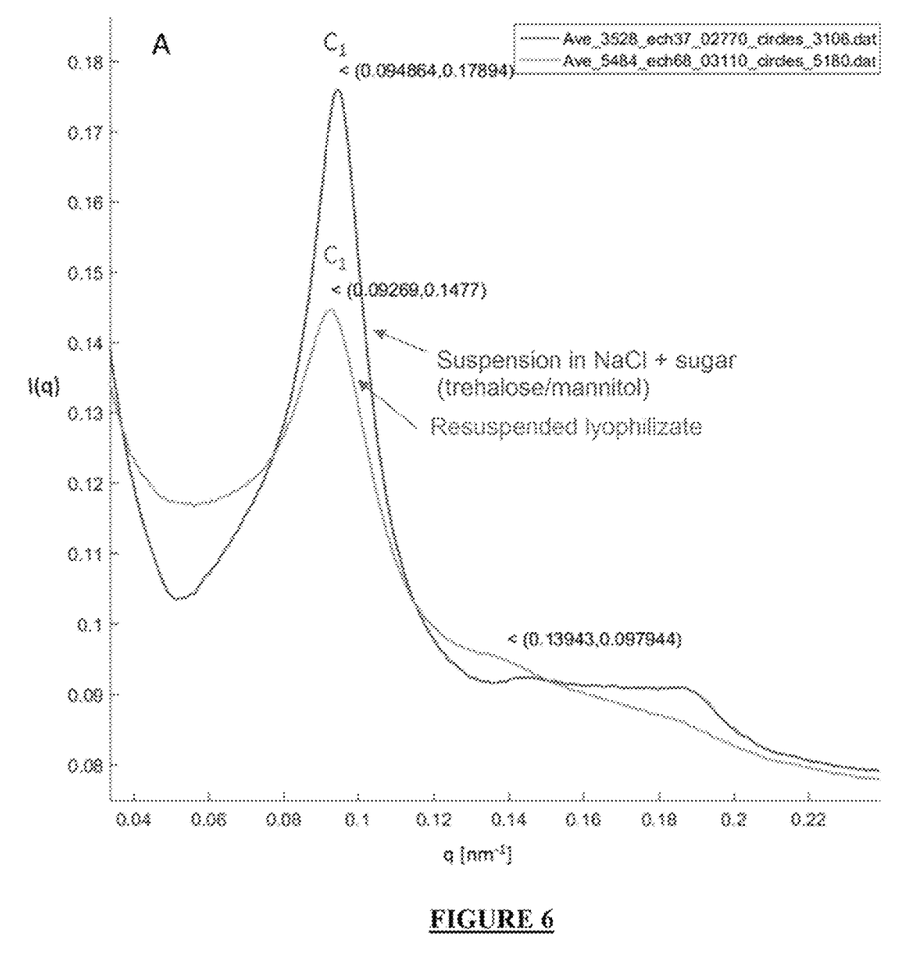

We then analysed the SAXS profile of the resuspended freeze-dried or compressed samples. The previous analysis having shown the influence of the presence of excipients on the structure of the particles (FIG. 5), we compared each resuspended sample with suspended lipoplexes under the same conditions of excipient concentration. The results obtained are presented in FIG. 6. It can be seen that the SAXS profile of the resuspended freeze-dried sample is close to the profile of suspended lipoplexes under the same conditions (FIG. 6A), which suggests that freeze-drying does not modify the structure of the lipoplexes. In the presence of an excipient, only a cubic phase is detected. On the other hand, for the resuspended compressed sample, the profile obtained makes it possible to clearly detect two phases, a lamellar and a cubic, whose main peaks have positions similar to those obtained for the initial lipoplex suspension (FIG. 3). The profile of this sample is distinctly different from that of a lipoplex suspension under identical conditions of excipient concentration. It is also different from the initial lipoplex suspension, since the relative proportion of the cubic and lamellar phases is reversed. In the initial suspension, the cubic phase is the majority, in the resuspended compressed sample, the lamellar phase is the majority. This result suggests that compression influences the structure by changing the relative proportion of one phase to the other, without however causing a new phase to appear or disappear.

Example 5: Evaluation of In Vivo Efficacy

Model: Induction of ulcerative colitis in mice by administration of dextran sulphate (DS) in drinking water for 7 days. Evaluation of Vector Efficacy: Oral administration of tablets containing siRNA lipoplexes. The tablets are given on days 1, 3 and 5 to mice under DS treatment (started on day 0). Each mouse receives a tablet containing 50 μg of siRNA formulated as lipoplexes.

Three groups of 10 mice are used:
Group 1: water drink, no lipoplex administration
Group 2: DS drink, on days 1, 3 and 5, tablet containing siRNA lipoplexes directed against TNF-α
Group 3: DS drink, on days 1, 3 and 5, tablet containing control siRNA lipoplexes (without inhibitory effect)
Group 4: DS drink, no lipoplex administration During treatment, weight and appearance of the faeces (presence of blood) are monitored. On day 7, euthanasia, collection of the colon, measurement of colon size, assay of inflammatory cytokines on a colon lysate, histological analysis of inflammation and tissue damage on colon sections.

Expected Result:

Decrease or even disappearance of clinical and biochemical signs of the disease following treatment. This decrease is specific to the siRNA sequence, i.e., it is observed in mice treated with lipoplexes containing anti-TNF-α siRNA and not in those treated with lipoplexes containing control siRNA.

The invention claimed is:

1. A process for the manufacture of a tablet comprising a complex between:
   (i) a nucleic acid which is a mRNA; and
   (ii) a lipid particle comprising a cationic lipid;
   said process comprising the following steps:
   a) drying an aqueous mixture comprising:
      a complex between (i) a nucleic acid and (ii) a lipid particle comprising a cationic lipid; and
      one or more excipient(s) suitable for drying, wherein the excipient suitable for drying comprises trehalose;
   b) mixing one or more compression excipient(s) with the dry mixture obtained in step a), wherein said one or more compression excipient(s) comprise magnesium stearate, optionally mixed with a diluent; and
   c) compressing the mixture obtained in step b) to form a tablet.

2. The process according to claim 1, wherein the lipid particle is a liposome or a micelle.

3. The process according to claim 1, said drying comprising freeze drying of the aqueous mixture.

4. The process according to claim 1, wherein the cationic lipid is selected from lipopolyamines, quaternary ammoniums, or lipids having a cationic head of the guanidine or imidazole type optionally mixed with a neutral lipid.

5. The process according to claim 4, wherein the cationic lipid is selected from Di-Myristylaminopropylaminopropyl (DMAPAP), N-[1-(2,3-dioleyloxy)propyl]-N,N,N-trimethylammonium chloride (DOTMA), [1,2-bis(oleoyloxy)-3-(trimethylammonio)propane] (DOTAP), 3β[N—(N',N'-dimethylaminoethane)-carbamoyl]cholesterol (DCChol) and dioctadecylamidoglycylspermine (DOGS); the cationic lipid being optionally mixed with a neutral lipid, selected from 1,2-dioleoyl-sn-glycero-3-phosphoethanolamine (DOPE), cholesterol, dioleoyl-sn-glycero-3-phosphocholine (DOPC), dipalmitoyl-sn-glycero-3-phosphocholine (DPPC) or N'-(rac-1-[11-(F-octyl)undec-10-enyl]-2-(hexadecyl)glycero-3-phosphoethanoyl)-sperminecarboxamide).

6. The process according to claim 4, wherein the mixture of the cationic lipid and the neutral lipid comprises:
   between 50 and 99 mol % cationic lipid in the mixture;
   between 1 and 50 mol % neutral lipid in the mixture.

7. The process according to claim 1, wherein the charge ratio (+/−) between the positive charges of the cationic lipid and the negative charges of the nucleic acid is between 0.5 and 10.

8. The process according to claim 1, wherein the excipient suitable for freeze-drying is trehalose optionally mixed with mannitol.

9. The process according to claim 1, wherein that the compression excipient(s) protect the complex between the nucleic acid and the lipid particle comprising the cationic lipid during the compression step c).

10. The process according to claim 9, wherein the compression excipient is a lubricant that represents from 0.25 to 5 mass % of the finished tablet.

11. The process according to claim 1, wherein the compression of step c) is carried out at a pressure between 10 and 400 MPa.

12. A tablet obtained by the process according to claim 1.

13. A tablet comprising:
   a complex between a nucleic acid, which is a mRNA, and a lipid particle comprising a cationic lipid;
   trehalose; and
   magnesium stearate, optionally mixed with a diluent.

14. The process according to claim 1, wherein the one or more excipient(s) is suitable for freeze-drying.

15. The process according to claim 1, wherein magnesium stearate is mixed with a diluent comprising lactose.

16. The process according to claim 1, wherein said one or more compression excipient is magnesium stearate mixed with a diluent comprising lactose and magnesium stearate composes from 0.25 to 5 mass % of the finished tablet.

17. The process according to claim 1, wherein the lipid particle comprises DMAPAP and DOPE and said one or more compression excipient is magnesium stearate mixed with a diluent comprising lactose.

18. The tablet according to claim 13, said tablet comprising:
   a complex between a nucleic acid and a lipid particle comprising a cationic lipid;
   trehalose; and
   magnesium stearate mixed with a diluent comprising lactose.

19. The tablet according to claim 13, said tablet comprising:
   a complex between a nucleic acid and a liposome or micelle comprising a cationic lipid;
   trehalose; and
   magnesium stearate, optionally mixed with a diluent comprising lactose.

* * * * *